United States Patent [19]

Okawa et al.

[11] Patent Number: 4,736,638

[45] Date of Patent: Apr. 12, 1988

[54] LIQUID LEVEL SENSOR

[75] Inventors: Dobson Okawa, Anaheim; Wing S. Pang, West Covina; Peter Kan, Fullerton, all of Calif.

[73] Assignee: Beckman Instruments, Inc., Fullerton, Calif.

[21] Appl. No.: 87,179

[22] Filed: Aug. 19, 1987

Related U.S. Application Data

[63] Continuation of Ser. No. 811,946, Dec. 20, 1985, abandoned.

[51] Int. Cl.$^4$ ............... G01N 35/06; G01F 23/00
[52] U.S. Cl. ............................. 73/864.24; 73/304 C
[58] Field of Search ........... 73/864.23, 864.25, 863.01, 73/304 C, 304 R, 290 R, 864.24; 340/620; 361/284; 422/63, 64, 100; 116/227; 200/199; 137/312; 324/61 P, 65 P

[56] References Cited

U.S. PATENT DOCUMENTS

| | | | |
|---|---|---|---|
| 3,687,632 | 8/1972 | Natelson | 73/864.25 |
| 4,276,258 | 6/1981 | Ginsberg et al. | 422/64 |
| 4,389,900 | 6/1983 | Gutierrez | 324/61 P |
| 4,615,351 | 10/1986 | Schliefer et al. | 73/304 R |

FOREIGN PATENT DOCUMENTS 1287148 8/1972 United Kingdom ............ 73/304 R

Primary Examiner—Stewart J. Levy
Assistant Examiner—Robert R. Raevis
Attorney, Agent, or Firm—William H. May; Arnold Grant; Gary T. Hampson

[57] ABSTRACT

Apparatus for sensing liquid levels in fluid transfer mechanisms and the like comprises a conductive member supporting containers for sample liquids, the conductive member being rotatably mounted for positioning selected containers under a conductive pipette probe. A low-frequency oscillator is capacitively coupled to the conductive member for generating an alternating electric field and producing an electrical signal at the probe. As the probe is lowered toward the liquid, an amplifier circuit monitors an electrical signal received by the probe. When the probe contacts the liquid, the amplifier detects a signal level in excess of a threshold level and produces an output signal for inhibiting the downward movement of the probe at the moment of contact with the liquid.

7 Claims, 1 Drawing Sheet

U.S. Patent
Apr. 12, 1988
4,736,638
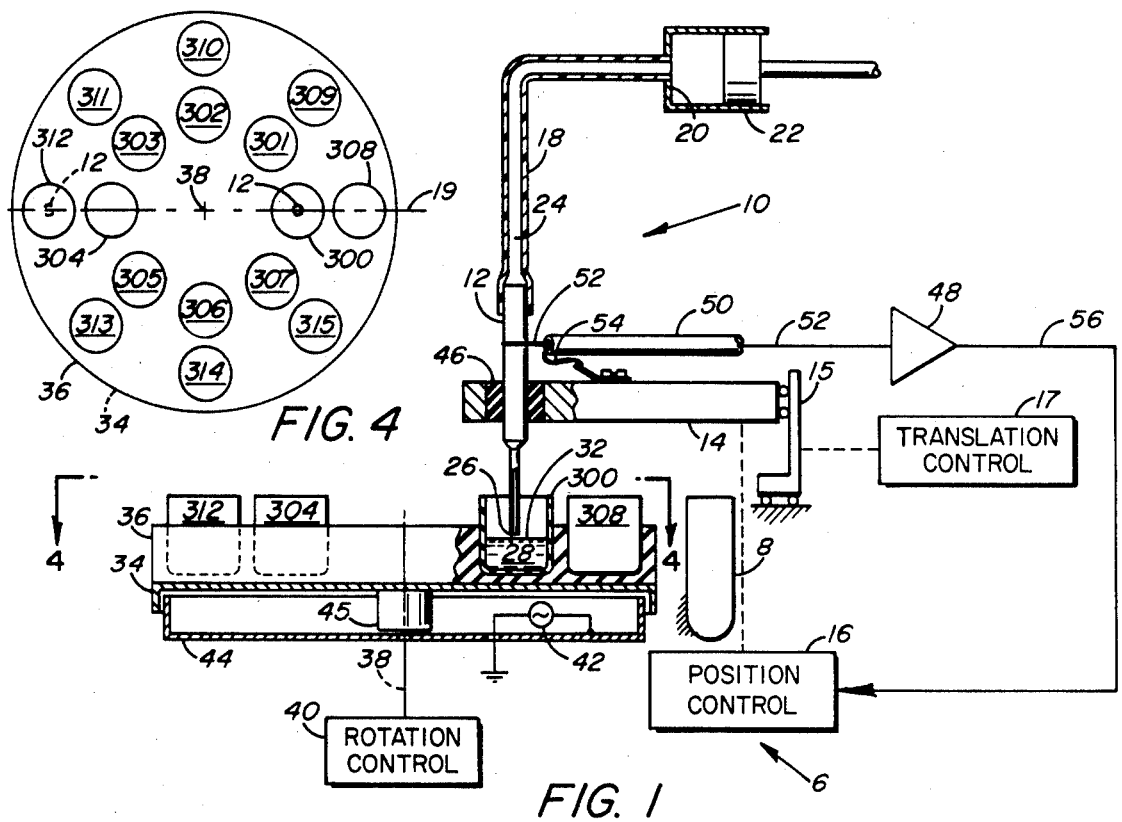
FIG. 4
FIG. 1
FIG. 3
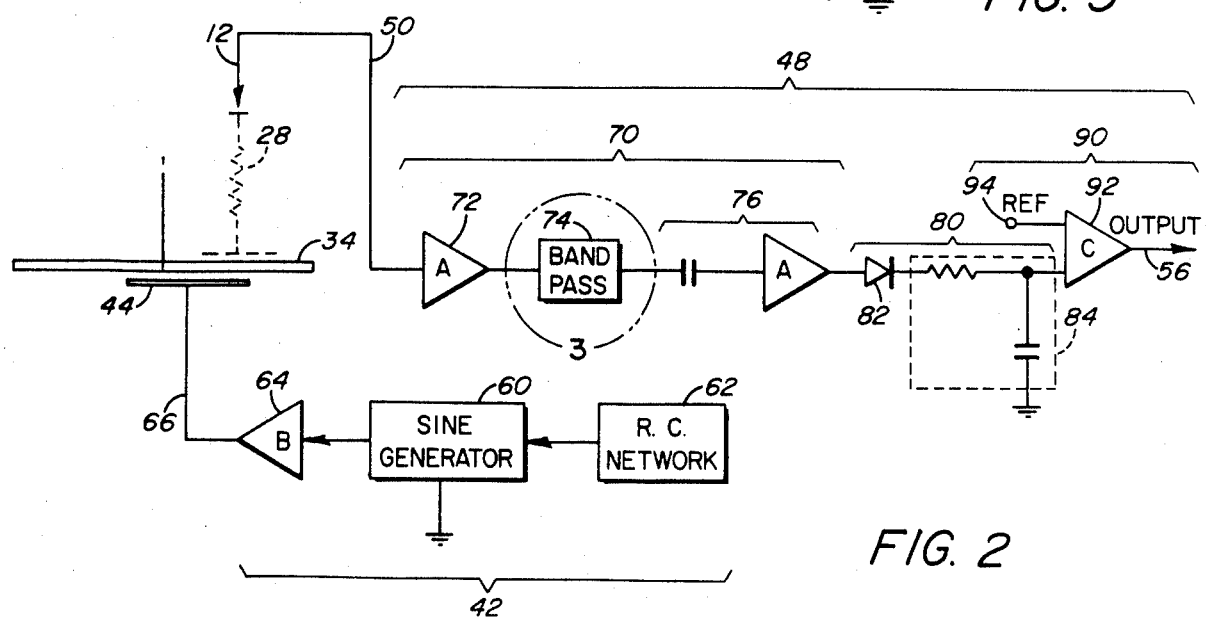
FIG. 2

LIQUID LEVEL SENSOR

This is a continuation of a co-pending application Ser. No. 811,946, filed on Dec. 20, 1985, now abandoned.

BACKGROUND

The present invention relates to fluid transfer systems, and more particularly to the transfer of liquids by pipette such as in chemical analyzers and mixing apparatus.

In a conventional pipette liquid transfer system, the pipette is lowered into contact with a sample liquid in a first container, a measured volume of the liquid ia drawn into the pipette, the pipette is raised and positioned over a second container, and the liquid is dispensed into the second container. The chemical analyzers typically process clinical samples from patients whose medical condition is being diagnosed. Thus a limited quantity of each sample is available and the analysis must be highly accurate and reliable. In order to transfer a small, precisely measured volume or aliquot of the liquid from a small sample, it is important that the pipette be very small in size and lowered only far enough to maintain contact with the liquid.

Such conventional systems exhibit various disadvantages, such as the following. In some apparatus, a pair of electrical probes is lowered with the pirpette into the container for sensing the liquid level. The pipette and multiple probes, each contacting the liquid, can pick up large, random, unmeasured quantities of the liquid, causing measuremenr errors. The combination of the pipette and the probes is bulky, requiring a large container that exposes a large surface area of the liquid to contamination; moreover, the combination is expensive to build and hard to align.

In other conventional apparatus, a probe is excited in a capacitive bridge circuit, a probe voltage being attenuated wnen the probe contacts a liquid that is capacitively coupled to ground. Other sensitive devices in the analyzer and nearby instruments are thus subject to electrical interference. These circuits are also sensitive to stray capacitances associated with the apparatus and external sources such as the hand of an operator of the apparatus. Further, they have a cumbersome alignment procedure that requires balancing of the bridge circuit. Thus the skill of an operator is a major factor in the speed and accuracy of the apparatus.

In an effort to solve some of these problems, further apparatus has the probe grounded for loading an oscillator when the probe contacts a liquid that is capacitatively coupled to the oscillator. The sensivity is reduced because the oscillator output changes only relatively slightly when the liquid contacts the probe. Consequently, elaborate circuits are used in this apparatus.

Thus there is a need for a level sensor for liquid transfer apparatus that reliably and precisely senses contact between a pipette and a sample liquid, and is simple and inexpensive to manufacture.

SUMMARY

The level sensor of the present invention meets this need by providing a source of low-frequency radiation beneath the liquid and a single electrically isolated pipette-probe that does not receive any substantial signal from rhe source when the probe is not contacting the liquid but receives a much higher level signal when the probe comes into contact with the liquid. The apparatus includes a source of AC, capacitively coupled to the liquid, and an AC detector for detecting increased AC at the probe when the probe comes into contact with the liquid.

In accordance with another aspect of the invention, a stationary source of AC is capacitively coupled to a moveable support for a plurality of liquid containers, the AC being retransmitted from the support through the liquid to a probe for sensing the liquid level in a selected one of the containers.

DRAWINGS

These and other features, aspects, and advantages of the present invention will become better understood with reference to the following description, appended claims, and accompanying drawings where:

FIG. 1 is a fragmentary sectional elevational view of a reaction analyzer incorporating level-sensing liquid transfer apparatus according to the present invention;

FIG. 2 is an electrical schematic diagram of the apparatus of FIG. 1;

FIG. 3 is a detailed portion of the diagram of FIG. 2 in region 3 of FIG. 2; and FIG. 4 is a fragmentary sectional elevational view of the apparatus of FIG. 1 taken on line 4–4 in FIG. 1.

DESCRIPTION

The present invention is directed to apparatus for sensing liquid levels in a fluid transfer mechanism such as in a chemical reaction analyzer. With reference to FIG. 1, a chemical analyzer 6 includes a reaction cell 8 and a pipette fluid transfer system 10 for delivering selected liquids to the reaction cell 8 for chemical analysis.

The transfer system 10 includes a tubular conductive probe 12 vertically mounted on a vertically movable arm 14, the arm 14 being horizontally located on a carriage 15. A position control or elevator 16, connected to the arm 14, controls the vertical position of the probe 12. A translation control 17, connected to the carriage 15, controls the horizontal position of the arm 14, the probe 12 being moveable along a probe path 19.

The probe 12 is connected by a flexible tubular conduit 18 to a measuring chamber 20 within a fluid valve actuator 22, shown in schematic form. The probe 12, the conduit 18, and the measuring chamoer 20 are filled with a liquid transport fluid 24 for effectively coupling the valve actuator 22 to a bottom tip 26 of the probe 12.

The probe 12 is positioned over a liquid sample 28, the sample 28 having a top surface 32. The sample 28 is confined in a selected container 300, the container 300 being one of an array of containers 300–315.

With further reference ro FIG. 4, the containers 300–315 are supported on a movable platter 34 in a rack 36, the rack 36 locating the containers 300–315 in a fixed relation to the platter 34. The platter 34 is rotatably mounted on a vertical platter axis 38 and provided with a rotation control or platter drive 40 for rotationally positioning the rack 36 under the probe 12. Thus the container 300 is defined by both the rotation of the rack 36 and the position of the probe 12 along the probe path 19.

Because it is desirable to rapidly move the probe over another of the containers 301–315, the translation control 17 is advantageously capable of moving the probe 12 across the platter axis 38 to, for example, the containers 304 and 312.

As shown in FIG. 4, the platter 34 is circular and concentric with the platter axis 38 for uniform distribution of antenna radiation toward the containers 300-315, independently of the rotational position of the platter 34.

An oscillator 42 is capacitively coupled to the platter 34 for producing an alternating electric field radiating upwardly through the sample 28 toward the probe 12, the platter 34 functioning as an antenna. The oscillator 42, referenced to a source of ground potential, is connected to a pan 44, the pan 44 being in close proximity to a hub 45 of the platter 34 for providing the capacitive coupling, the platter 34 and the pan 44 being otherwise electrically isolated.

Thus the pan 44 radiates an AC signal to the platter 34, the platter 34 retransmitting the AC signal to the probe 12 through the liquid sample 28. Accordingly, the present invention provides a moving antenna for supporting and exciting the containers 300-315, the antenna being driven from a stationary source without requiring sliprings, flexible where connections, or other cumbersome and unreliable devices.

Tne platter 34, retransmitting the AC from the oscillator 42 to each of the containers 300-315, advantageously permits rapid movement of the probe 12 trom a previously selected container, such as the container 312, to the selected container 300 along the probe path 19, passing over the platter axrs 38, the apparatus being capable of sensing the liquid level in any of the containers 300-315 thar are positioned along the probe path 19.

With further reference to FIG. 2, the oscillator 42 includes a signal generator 60 naving an associated resistor-capacitor network 62. The network 62 configures the signal generator 60 for producing a continuous constant amplitude sine wave at a frequency of approximately 5 KHz, the sine wave output of the signal generator 60 being amplified by a buffer 64, the buffer 64 being directly coupled to the signal generator 60 and having an oscillator output 66 for driving rhe platter 34 as described above. The oscillator output 66 produces a smooth sine wave having a peak-to-peak amplitude of approximately 20 volts. The oscillator 42 is conveniently mounted in a fixed position on the pan 44 under the platter 34.

The smooth sine wave output at the 5 KHz frequency conveniently and reliably avoids the production of electromagnetic radiation at frequencies at or above 10 KHz that are subject to FCC and other governmental regulations. More importantly, the relatively low 5 KHz frequency does not interfere with nearby sensitive analyzer circuits (not shown) that are associated with the transfer system 10. The 5 KHz frequency is not critical, however. A sufficiently high frequency for adequate capacitive coupling is approximately 4.0 KHz. A sufficiently low frequency for safely avoiding the 10 KHz limitation is approximately 9.0 KHz. Thus a preferred embodiment of the present invention provides an oscillator frequency of from approximately 4.0 KHz to approximately 9.0 KHz.

The probe 12, electrically isolated from the arm 14 by a tubular insulating member 46, is connected to a detector 48 by a coaxial cable 50. The coaxial cable 50 has a signal lead 52 connected to the probe 12 and a shield lead 54 connected to the arm 14. Tne detector 48, further described below, is connected to the elevator 16 by an output lead 56 for inhibiting downward movement of the probe 12 when contact is established with the sample 28 as determined by the detector 48.

The detector 48 includes an amplifier section 70 for receiving the electrical signal from the probe 12. The amplifier section 70 comprises a preamplifier 72, a band pass filter 74, and a decoupling amplifier 76. The preamplifier 72 provides a broadband gain of approximately 1,000 for amplifying the very low level signals present at the probe to a convenient amplitude for further processing.

With further reference to FIG. 3, the band pass filter 74 is a circuit for rejecting unwanted signals ar frequencies outside a frequency range that includes the frequency of the oscillator 42. Tne band pass filter 74 is an active single-pole circuit including a filter amplifier 741, an input resistor 742, a series resistor 743 connected between the input resistor 742 and a non-inverting input 744 of the filter amplifier 741, a grounded lag capacitor 745 loading the non-inverting input 744. A lead capacitor 746 couples the connection of the input resistor 742 and the series resistor 743 to an inverting input 747 of the filter amplifier 741, the inverting input 747 also having direct feedback from an output 748 of the filter amplifier 741. Thus the band pass filter 74 passes signals from the preamplifier 72 to the decoupling amplifier 76 at frequencies within a range of approximately 4.5 KHz to approximately 5.5 KHz that includes the 5 KHz frequency of the oscilator 42, attenuating frequencies outside the range for rejecting unwanted signals received at the probe 12.

The decoupling amplifier 76 is capacitively coupled to the band pass filter 74 for removing any undesirable offset voltage that may have been introduced by the preamplifier 72 and/or the band pass filter 74. The decoupling amplifier 76 provides a further gain of approximately 5 within the frequency range of the band pass filter 74.

The detector 48 also comprises a converter section 80 for receiving the amplified AC signal from the decoupling amplifier 76 and producing a unipolar DC voltage corresponding to the amplitude of the electrical signal received at the probe 12.

The detector 48 also includes a comparator section 90 for driving the output lead 56 in response to the converter section 80. The comparator section 90 includes a comparator circuit or threshold detector 92 having a fixed voltage reference 94 for determining whether the electrical signal received at the probe 12 exceeds a threshold signal level. Thus when the probe 12 is not in contact with the sample 28, the signal received by the probe 12 is below the threshold level, and the converter section 80 does not produce a DC level sufficient to exceed the the reference 94. Correspondingly, a first logic level is produced by the comparator section 90 at the output lead 56, the first logic level permitting operation of the elevator for lowering the probe 12.

When the probe 12 comes in contact with the sample 28, a high level electrical signal is received at the probe 12 from the oscillator 42, resulting in a corresponding DC voltage from the converter section 80, the DC voltage exceeding the reference 94 and causing a second logic level to appear at the output lead 56, the second logic level inhibiting the elevator 16 for preventing further downward movement of the probe 12 into the container 300.

The apparatus of the present invention reliably and accuratly detects contact between the probe 12 and the sample 28 without requiring a plurality of electrodes in the container. Thus the prooe 12, functioning as a pipette as well as a single electrode, does not require a large container that would expose a large area of the sample to contamination. Further, the tip 26 of the probe 12, not being encumbered by separate electrode elements, need only be large enougn to receive an aliquot of the sample 28. Thus the probe 12 is not subject to picking up large, random, unmeasured quantities of the sample 28 that would otherwise interfere with the transfer of a precisely measured aliquot, corrupting analysis of the sample 28.

An important feature of the present invention is that the detector 48 receives little or no signal from the probe 12 until there is contact of the probe 12 with the liquid sample 28. When contact occurs, the detector 48 receives a greatly increased signal that is easy to detect because there is a large signal ratio between the contact and out-of-contact conditions.

The platter 34, by providing in a single moveable element both an antenna and supporting structure for the containers 300-315, permits the oscillator output to be uniformly coupled to each of the containers 300-315, regardless of the rotational position of the rack 36. Thus valuable positioning time can be saved in a statistically significant percentage of moves of the probe 12 with respect to the containers 300-315 by permitting the probe 12 to move across the platter axis 38. This is because the probe 12 can be safely and/or more easily accelerated laterally than can all of the containers 300-315, and the path of rne probe, moving alone, is often shorter than a corresponding container path.

In an experimental version of the present invention, it has been determined that the detector 48 reliably signals contact between the probe 12 and the top surface 32 of the sample 28, even when the sample 28 is deionized water that is located above the platter 34 at a distance of up to approximately 25 mm.

Preferably the distance between the platter 34 and the sample 28 is not more than approximately 20 mm for assuring high accuracy and reliability in ordinary use.

In operation, the probe 12 is positioned over the selected container 300 by the translation control 17 and the rotation control 40 as described above, after raising the tip 26 of the probe 12, if necessary, higher than the tops of the containers 300-315 by the elevator 16. Once positioned, the probe 12 is lowered into the container 300 at a controlled rate of speed by the elevator 16. It should be understood that the controlled rate of speed can be an incremental rate such as provided by conventional stepper control.

While the probe 12 is being lowered into the container 300, the oscillator 42 is powered for driving the pan 44 with the 5 KHz alternating current. The alternating current is capacitiely coupled into the platter 34 by the hub 45, the platter 34 capacitively retransmitting the 5 KHz oscillator signal to the sample 28. Until the probe 12 touches the top surface 32 of the sample 28, very little, if any, of the oscillator signal is received by the probe 12, because the oscillator signal must pass through air between the top surface 32 of the sample 28 and the probe 12. Thus the first logic level is produced at the output lead 56, permitting further downward movement of the probe 12 by the elevator 16, as described above.

When the tip 26 of the probe 12 makes contact with the liquid sample 28, there is a large increase in the signal received by the probe 12, because there is no longer air space between the probe 12 and the top surface 32 of the sample 28, and because a relatively large equivalent surface area of the sample 28 is capacitively coupled to the platter 34. The signal received by the probe 12 is amplified and detected in the detector 48, as described above, causing the second logic level to be produced at the output signal 56 as described above. Further downward movement of the probe 12 is thus inhibited by the second logic level on the output lead 56 as described above, the tip 26 of the probe 12 just touching the top surface 32 of the sample 28.

Thus an aliquot of the sample 28 can be drawn into the probe 12 by the valve actuator 22 so that the aliquot, and a desired amount of the transport fluid 24 can be deposited into the reaction cell 8 for analysis.

Although the present invention has been described in considerable detail with reference to certain preferred versions thereof, other versions are possible. For example, the oscillator 42 can be connected directly to the platter 34, rather than the pan 44, by a flexible lead, sliding contact, or other suitable means. Therefore, the spirit and scope of the appended claims snould not necessarily be limited to the description of the preferred versions contained herein.

What is claimed is:

1. Apparatus for detecting physical contact between a conductive probe and an exposed surface of one of a plurality of liquid samples held in sample containers, the apparatus comprising:
   (a) an oscillator including means for generating an alternating current signal;
   (b) a stationary capacitive coupling member;
   (c) means for coupling the alternating current signal to the stationary capacitive coupling member;
   (d) a conductive member supporting the containers and disposed proximate the stationary capacitive coupling member whereby the alternating current signal is coupled to the conductive member and the conductive member couples the alternating current signal to all of the liquid samples supported by the conductive member;
   (e) conductive member support and drive means for moveably supporting the conductive member and moving the conductive member and the containers disposed on the conductive member with respect to the stationary capacitive coupling member;
   (f) amplifier means coupled to the probe for amplifying a signal received by the probe, the signal received by the probe including a signal produced by the alternating current signal; and
   (g) means responsive to the amplifier means for detecting a threshold level of the alternating current signal received by the probe indicative of contact between the probe and one of the liquid samples.

2. The apparatus of claim 1 wherein the means for generating the alternating current signal generates such signal at a frequency of less than 10 KHz.

3. The apparauts of claim 2 wherein the means for generating the alternating current signal generates such signal at a frequency between 4.0 KHz and 9.0 KHz.

4. The apparatus of claim 1 wherein the amplifier means comprises band pass filter means for rejecting signals other than the signal produced by the alternating current signal.

5. The apparatus of claim 1 wherein the conductive member is separated from the liquid samples by a distance of less than 20 mm.

6. The apparatus of claim 1 whrein the conductive member is circular and is disposed horizontally and the support and drive means includes means for rotatably supporting the conductive member about a central vertical axis of the conductive member.

7. The apparatus of claim 1 wherein the apparatus includes means for moving the probe along a path above the sample containers.

* * * * *